(12) United States Patent
Hayashihara

(10) Patent No.: US 8,135,294 B2
(45) Date of Patent: Mar. 13, 2012

(54) IMAGE FORMING APPARATUS FOR FORMING IMAGE ON RECORD MEDIUM

(75) Inventor: Hiromichi Hayashihara, Yokohama (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/043,966

(22) Filed: Mar. 9, 2011

(65) Prior Publication Data

US 2011/0187809 A1    Aug. 4, 2011

Related U.S. Application Data

(63) Continuation of application No. 12/757,134, filed on Apr. 9, 2010, now Pat. No. 7,991,310, which is a continuation of application No. 11/735,726, filed on Apr. 16, 2007, now Pat. No. 7,715,740.

(51) Int. Cl.
*G03G 15/00* (2006.01)

(52) U.S. Cl. .......................................... 399/45; 356/601

(58) Field of Classification Search .................... 399/45, 399/388, 389; 356/445, 600, 601, 612, 606
See application file for complete search history.

(56) References Cited

U.S. PATENT DOCUMENTS

| | | | |
|---|---|---|---|
| 5,521,692 A | 5/1996 | Bares | |
| 6,386,676 B1 | 5/2002 | Yang et al. | |
| 6,894,262 B2 | 5/2005 | Gao et al. | |
| 7,483,158 B2 | 1/2009 | Hayashihara | |
| 7,715,740 B2 | 5/2010 | Hayashihara | |
| 2003/0194251 A1 | 10/2003 | Maruyama et al. | |
| 2004/0129901 A1 | 7/2004 | Yamaguchi et al. | |
| 2005/0280687 A1 | 12/2005 | Kurahashi | |
| 2006/0238592 A1 | 10/2006 | Kadomatsu et al. | |

FOREIGN PATENT DOCUMENTS

| | | |
|---|---|---|
| JP | 05-069993 | 3/1993 |
| JP | 11-184317 | 7/1999 |
| JP | 2003-205654 | 7/2003 |
| JP | 2004-050815 | 2/2004 |
| JP | 2006-58261 | 3/2006 |
| JP | 2006-168138 | 6/2006 |
| JP | 2006-184504 | 7/2006 |

OTHER PUBLICATIONS

Machine Translation of JP 05-069993 A dated Jan. 28, 2009.
Machine Translation of JP 2006-168138 A dated Jan. 28, 2009.
Machine Translation of JP 2006-184504 A dated Jan. 28, 2009.
Office Action for U.S. Appl. No. 11/735,726 mailed on Feb. 3, 2009.
Office Action for U.S. Appl. No. 11/735,726 mailed on Aug. 7, 2009.
Office Action for U.S. Appl. No. 12/757,134 mailed on Sep. 14, 2010.
Office Action for U.S. Appl. No. 12/757,134 mailed on Jan. 10, 2011.
Japanese Office Action for Japanese Application No. 2007-235272 mailed Jan. 17, 2012.

*Primary Examiner* — Sophia S Chen
(74) *Attorney, Agent, or Firm* — Turocy & Watson, LLP

(57) ABSTRACT

A record medium determining device 1, which determines a kind of a record medium 16 by irradiating a laser light 17 to a surface of the record medium 16, detecting a received light position and a received light intensity of a reflected light 18 by a line sensor 14, and comparing a distribution state of the received light position and the received light intensity with a previously determined distribution state, is disposed on the upstream side of a record medium conveyance path 653 with respect to a fixing unit.

3 Claims, 10 Drawing Sheets

IMAGE FORMING APPARATUS FOR FORMING IMAGE ON RECORD MEDIUM

CROSS-REFERENCE TO RELATED APPLICATIONS

This application is a Continuation of application Ser. No. 12/757,134 filed Apr. 9, 2010, which is a Continuation of application Ser. No. 11/735,726 filed Apr. 16, 2007, the entire contents of both of which are hereby incorporated by reference.

BACKGROUND OF THE INVENTION

1. Field of the Invention

The present invention relates to an image forming apparatus for forming an image on a record medium, which includes a record medium determining device to irradiate a laser light to the record medium, to detect a reflected light thereof, and to determine the kind of the record medium from the distribution state of the reflected light.

2. Description of the Related Art

In order to perform excellent image formation in an image forming apparatus such as a copier or a printer, it is necessary to adjust a printing method according to the kind of a record medium, such as a sheet, on which an image is formed. For example, unless the printing method is adjusted in a case where printing is performed on a plain paper and a case where printing is performed on an OHP sheet, an excellent image can not be obtained.

In an early model, although an operator manually selects the kind of a record medium, since there is a case where an erroneous selection is made, the development of a device to detect the kind of the record medium has been advanced.

In the related art, there is proposed a device in which a light is irradiated to a record medium, and a reflected light thereof and a transmitted light thereof are detected (for example, JP-A-2006-58261).

This is such that with respect to the light from a first light emitting source, the received light amount of the transmitted light is detected by a first light receiving element disposed at a position opposite to the first light emitting source across the record medium, and with respect to the light from a second light emitting source, the received light amount of the reflected light is detected by a light receiving element disposed on the same side as the second light emitting source with respect to the record medium, and these received light amounts are compared with threshold values to determine the kind of the record medium.

However, in this technique, there is a problem that although it is possible to determine record media, like an OHP sheet and a plain paper, in which the received light amounts of the transmitted lights and the received light amounts of the reflected lights are much different from each other, when the received light amounts of the transmitted lights and the received light amounts of the reflected lights become approximate to each other like a plain paper and a recycle plain paper, the accuracy of determination is reduced.

In order to solve this problem, there is proposed a device in which a light is irradiated to a record medium, and a reflected light thereof is detected by an area sensor (for example, JP-A-2003-205654).

This is such that the reflected light is received by a two-dimensional surface, an average value, a maximum value and a minimum value are calculated from the amount of received light, and they are compared with threshold values to determine the kind of the record medium.

However, as described later, in this technique, the range of the reflected light which can be received by the area sensor is limited, and there is a problem that the kind of the record medium which can be determined from the pattern of the detectable reflected light is limited.

BRIEF SUMMARY OF THE INVENTION

It is an object of the present invention to provide an image forming apparatus for forming an image on a record medium, which includes a record medium determining device to determine a kind of the record medium by irradiating a laser light to a surface of the record medium, detecting a received light position and a received light intensity of a reflected light thereof, and comparing a distribution state of the received light position and the received light intensity with a previously determined distribution state.

In an aspect of the present invention, an image forming apparatus for forming an image on a record medium includes a record medium determining device including a laser light source to irradiate a laser light to a surface of the record medium, a line sensor to receive a reflected light of the laser light from the record medium and to output an output signal converted into an electric signal, wherein the line sensor detects a received light position in the line sensor having received the reflected light and a received light intensity of the received reflected light from the output signal, and a signal processing device to determine a kind of the record medium by comparing a distribution state of the received light position and the received light intensity with a previously determined distribution state.

DETAILED DESCRIPTION OF THE INVENTION

Throughout this description, the embodiments and examples shown should be considered as exemplars, rather than limitations on the apparatus and methods of the present invention.

Hereinafter, an embodiment of a particle detecting apparatus of the invention will be described in detail by use of the drawings.

<Record Medium Determining Device>

First, a record medium determining device will be described.

Figure 1:
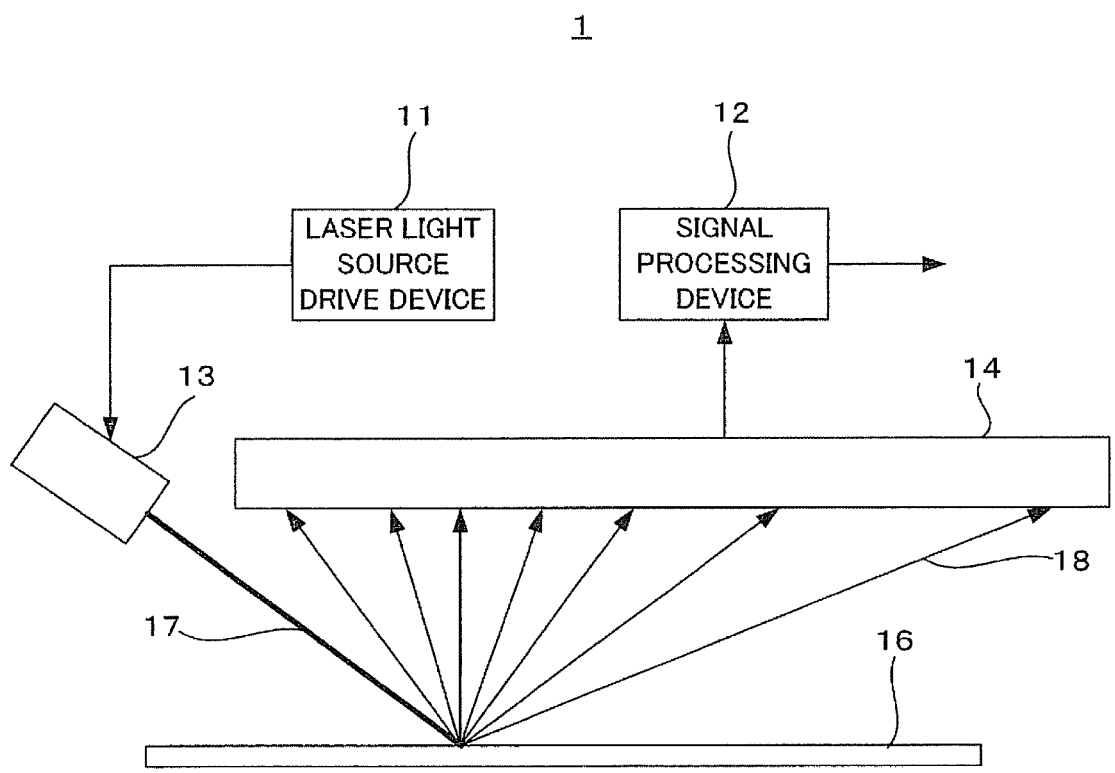
FIG. 1 is a structural view showing the outline of a record medium determining device.

FIG. 1 is a structural view showing the outline of the record medium determining device of an embodiment. The record medium determining device 1 of the embodiment includes a laser light source 13 to irradiate a laser light 17 to a surface of a record medium 16, a laser light source drive device 11 to supply power to the laser light source 13 and to control irradiation of the laser light 17, a line sensor 14 to receive a reflected light 18 of the laser light 17 reflected by the record medium 16 and to output an output signal converted into an electric signal, and a signal processing device 12 to receive the output signal, to perform a specified determination processing and to determine the kind of the record medium 16.

The laser light source 13 is a device to irradiate the laser light 17, and the kind of the laser light and the principle of the laser light oscillation are not restricted. Although the wavelength of the laser light 17 may be any wavelength as long as the after-mentioned line sensor 14 can detect, a visible light is desirable in view of handling. The intensity of the laser light 17 can be arbitrarily set within a range where it is reflected by the record medium 17 and reaches the line sensor 14 at such intensity that it can be detected by the line sensor 14.

Figure 2:
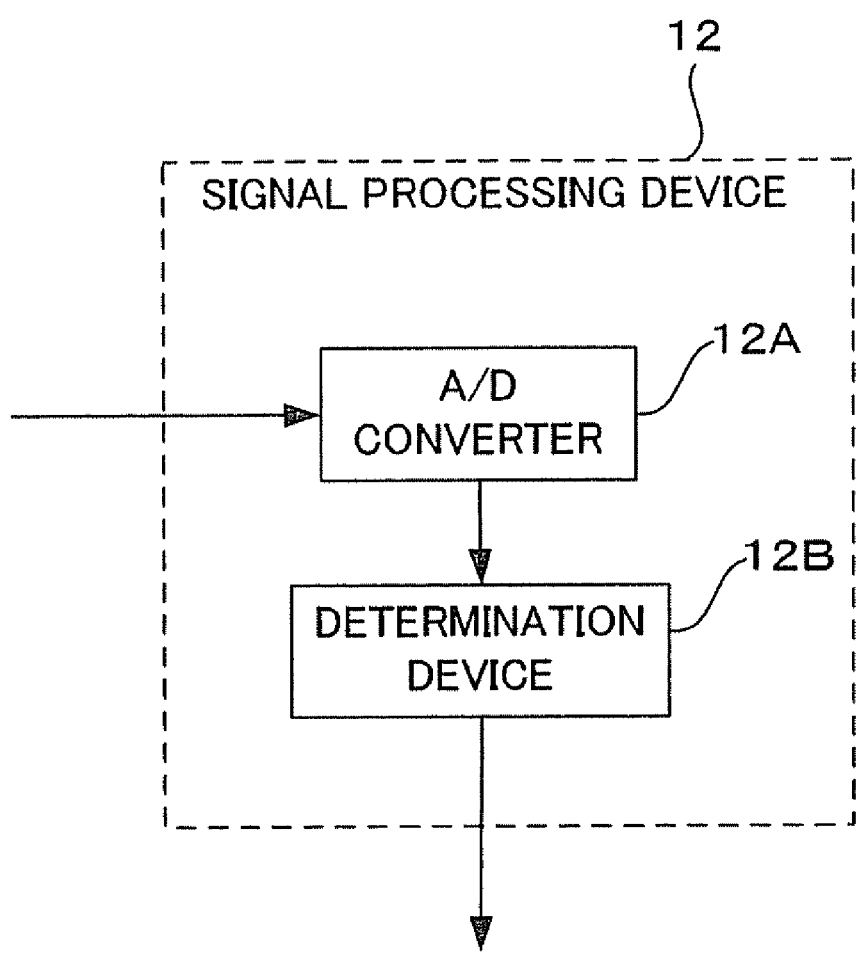
FIG. 2 is a view showing a structural example of a signal processing device.

FIG. 2 is a view showing a Structural example of the signal processing device 12. The signal processing device 12 includes an A/D converter 12A which receives the output signal from the line sensor 14 and converts analog data into digital data, and a determination device 12B to perform a specified processing on the output signal converted into the digital data and to output the kind of the record medium 16.

The determination device 12B can be constructed, for example, as described below. The determination device 12B includes a processor such as a digital signal processor, a memory to store data and a program, and a communication device to output data to an external device. This processor reads the program describing a processing procedure to determine the record medium 16 from the memory and executes it, so that the inputted output signal is processed, and the determination result is outputted.

Figure 3:
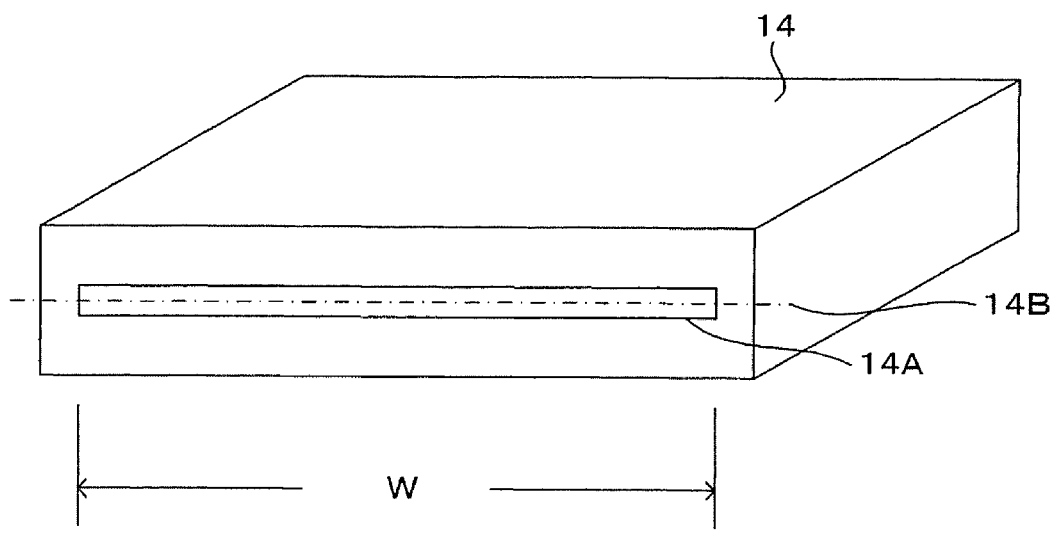
FIG. 3 is a view showing the outer appearance of a line sensor.

FIG. 3 is a view showing the outer appearance of the line sensor 14. The line sensor 14 includes, for example, a linear sensor 14A to receive a light and to convert it into an electric signal, and a conversion device to amplify and convert the electric signal converted by the sensor 14A to a state suitable for output.

As the sensor 14A, what is obtained by arranging plural optical sensors linearly may be used, or one vertically long optical sensor may be used. In the case where the plural optical sensors are used, the light sensors may be arranged in one line, may be arranged to be alternately shifted, or may be arranged in two or more lines.

In the case where the record medium determining device 1 of the embodiment is installed in an image forming apparatus to exclusively print the record medium 16 of a small size, it is necessary to use the smaller line sensor 14, and in the case where it is installed in an image forming apparatus, such as a copier, to print also the record medium of a large size, it is necessary to use the larger line sensor 14. As stated above, the width W of the sensor 14A in the longitudinal direction can be suitably selected according to the size of the record medium 16 to be determined.

From the background as stated above, it is desirable that the length of the sensor 14A of the line sensor 14 in the longitudinal direction is not less than 5 mm and not larger than the length of the maximum record medium to be determined in the longitudinal direction.

Figure 4:
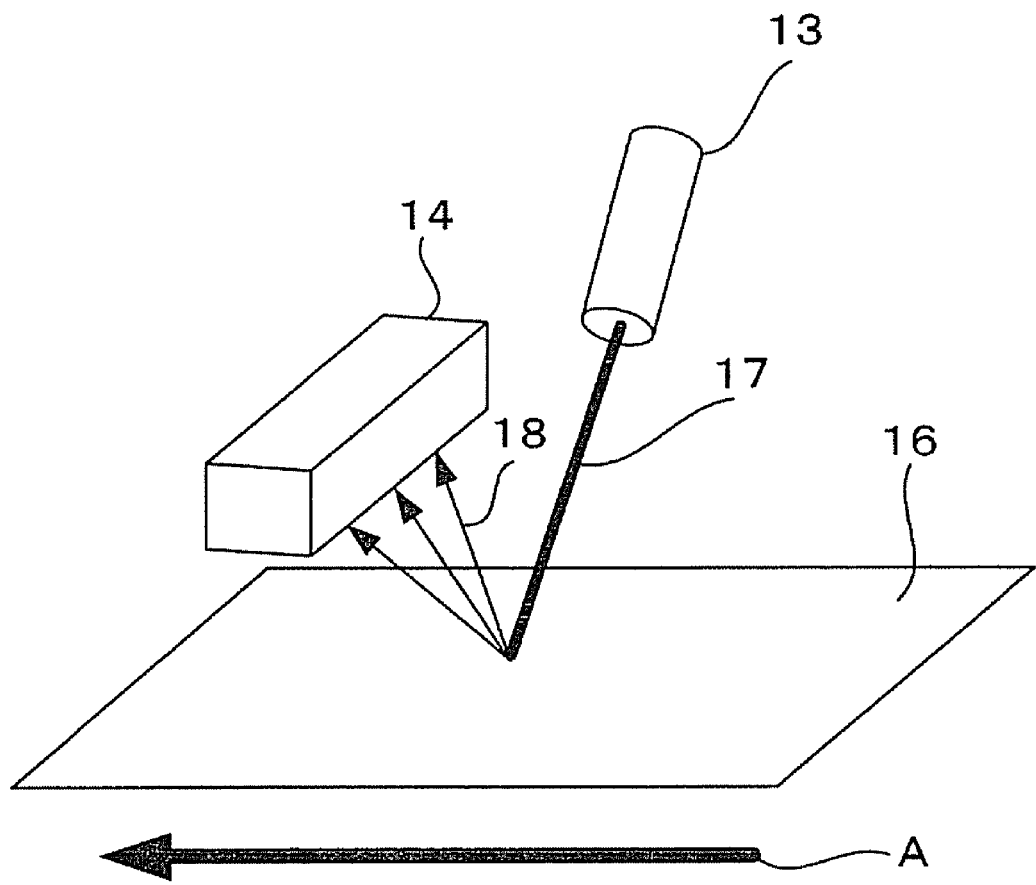
FIG. 4 is a view showing a positional relation among a laser light source, a line sensor, and a record medium.

FIG. 4 is a view showing a positional relation among the laser light source 13, the line sensor 14 and the record medium 16. The laser light source 13 and the line sensor 14 are disposed at the same side with respect to the record medium 16. The line sensor 14 is disposed at a position where the reflected light 18 of the laser light 17 irradiated from the laser light source 13 and reflected by the record medium 16 is incident on the sensor 14A.

It is desirable that the laser light source 13 and the line sensor 14 are disposed such that when the record medium 16 totally reflects the laser light 17, an axis of the sensor 14A of the line sensor 14 in the longitudinal direction is positioned on a plane to which light paths of the laser light 17 irradiated from the laser light source 13 and the reflected light 18 of the laser light 17 reflected by the record medium 16 belong. Here, the axis of the sensor 14A in the longitudinal direction is the center line of the light receiving surface of the sensor 14A in the longitudinal direction as designated by 14B in FIG. 3.

It is desirable that the plane to which the light paths belong is substantially vertical to the conveyance direction of the record medium 16 indicated by an arrow A.

Figure 5:
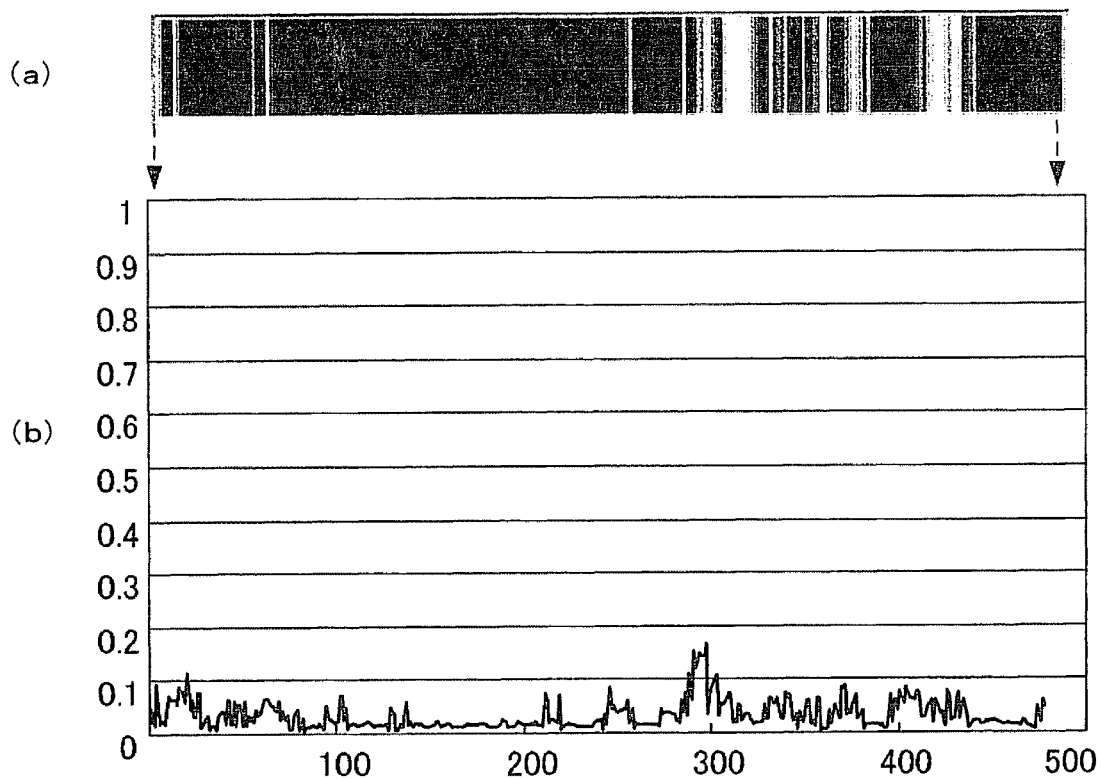
FIG. 5 is a view showing detection results of a case where a record medium is a recycled paper.

Next, detection results of the reflected light 18 in the line sensor 14 will be described. FIG. 5 is a view showing detection results of a case where the record medium 16 is a recycled paper. FIG. 5(b) is a graph in which the vertical axis indicates the intensity of the detected reflected light 18, the horizontal axis indicates the received light position in the sensor 14A of the line sensor 14 having received the reflected light 18, and the detection results are plotted.

FIG. 5(a) is a view showing the detection results in which at each received light position in the sensor 14A, a case of exceeding a threshold value is shown to be white ("1" when it is indicated by a numerical value), and a case of the threshold value or less is shown to be black ("0" when it is indicated by a numerical value). Incidentally, performing binarization means making an expression with two values with reference to a threshold value.

Here, a distribution state means a state indicated by the detected intensity of the reflected light 18 at each received light position in the sensor 14A of the line sensor 14 having received the reflected light 18.

In the case where the record medium 16 is such that the surface is not glossy and is rough like the recycled paper, the distribution state is such that the intensity of the reflected light 18 is low in total, and the reflected light 18 is detected in a wide range of the sensor 14A.

Figure 6:
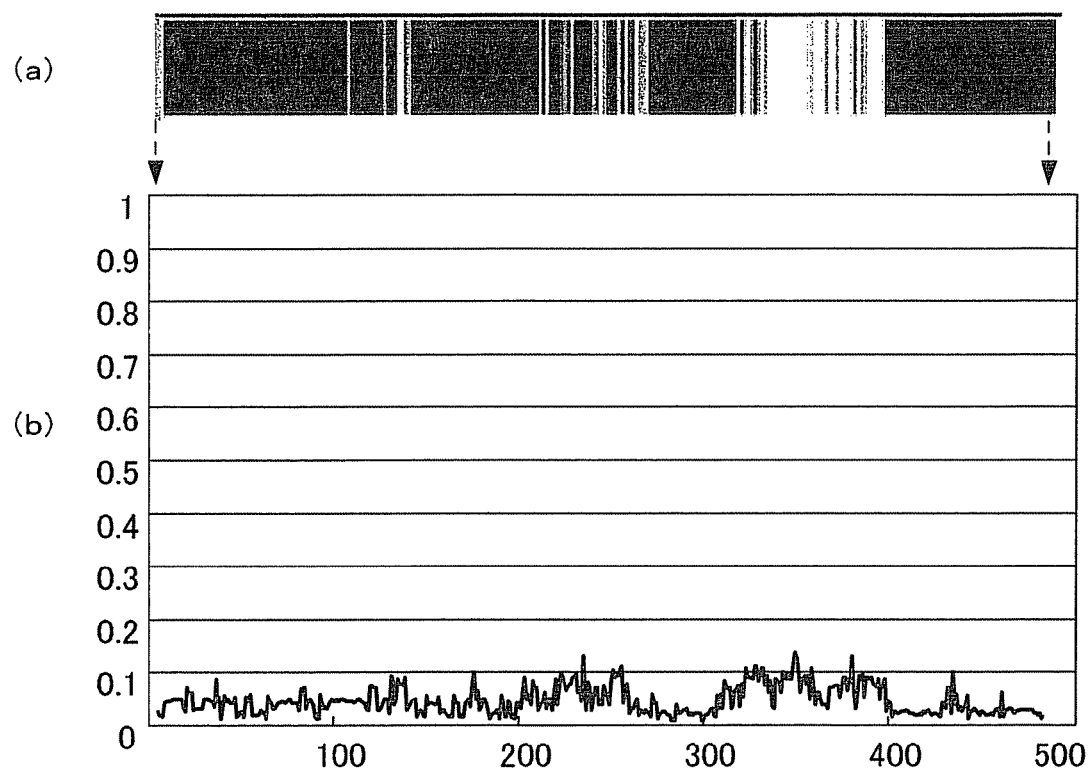
FIG. 6 is a view showing detection results of a case where a record medium is a plain paper.

FIG. 6 is a view showing, similarly to FIG. 5, detection results of a case where the record medium 16 is a plain paper. In the case where the record medium 16 is such that the surface is not glossy but is not very rough, the distribution state is such that the intensity of the reflected light 18 is rather high in total, and the reflected light 18 is concentrated on a portion of the sensor 14A and is detected.

Figure 7:
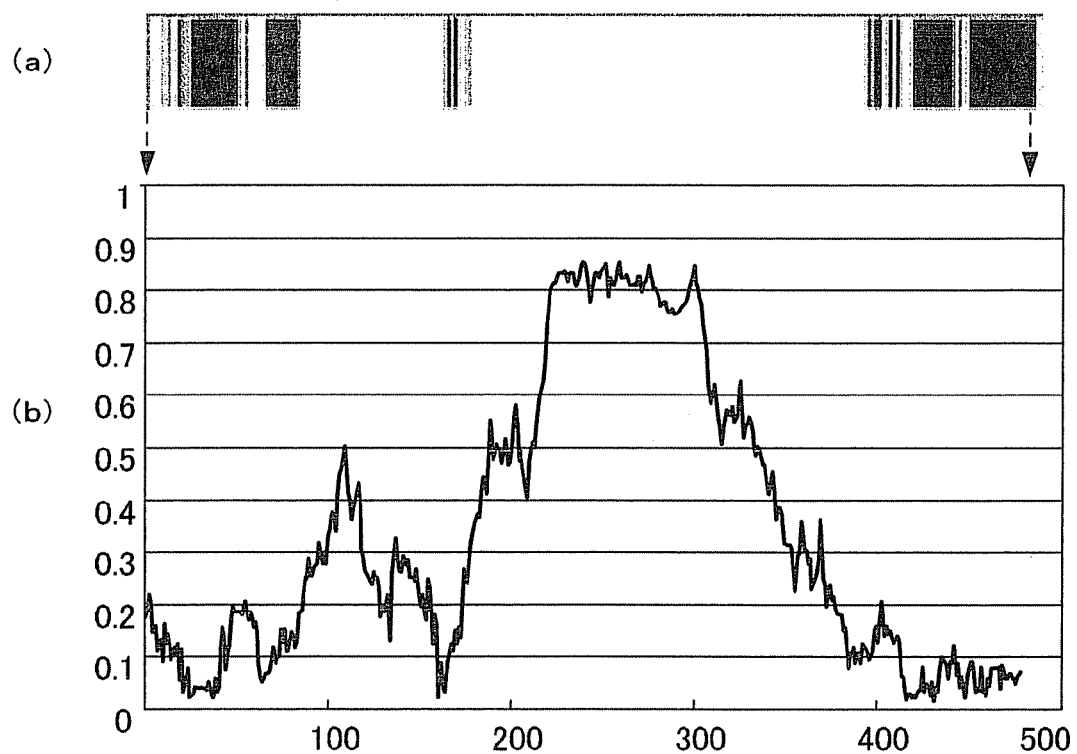
FIG. 7 is a view showing detection results of a case where a record medium is a glossy paper.

FIG. 7 is a view showing, similarly to FIG. 5, detection results of a case where the record medium 16 is a glossy paper. In the case where the record medium 16 is such that the surface is glossy and is not rough, the distribution state is such that the intensity of the reflected light 18 is very high in total, and the reflected light 18 is concentrated on the center portion of the sensor 14A and is widely detected.

As stated above, according to the embodiment, since the distribution state varies according to the kind of the record medium 16, the distribution state is compared with a previously determined distribution state, and the kind of the record medium 16 is determined.

Next, a specific determination method will be described. The determination method is not limited, and a well-known method or a newly contrived method can be suitably selected. Hereinafter, a description will be given to a method (first application example) in which a Euclid distance is compared, a method (second application example) in which a difference of detection values is compared, a method (third application example) in which at the time of conveyance of the record medium 16, the laser light 17 is irradiated for a definite time and a detected value is integrated, and a method (fourth application example) in which the detected value is averaged at each detection position and is compared.

First Application Example

The signal processing device 12 expresses detected values, that is, a distribution state by a vector. Each component may be a relative value of the detected value or a binarized numerical value of 0 or 1. A column represents a position on the sensor 14A.

In the case where there are eight detection positions and the binarized values are used, an example of a vector X of detected values becomes $X1=(0,1,0,0,1,1,0,0)$ $X2=(0,0,1,1,1,1,1,0)$.

Here, an example of a vector as reference, that is, a previously determined distribution state is made $S1=(0,1,0,0,1,0,0,0)$:recycled paper $S2=(0,1,1,1,1,1,1,0)$:glossy paper.

The values are stored in a memory of the signal processing device 12 as a table or a part of a program.

Next, a Euclid distance D(a, b) between two points $a(a1, a2, \ldots, an)$ $b(b1, b2, \ldots, bn)$ is defined as indicated below.

$$D(a, b) = \sqrt{\sum_{i=1}^{n} (ai - bi)^2}$$

Next, the signal processing device 12 sequentially obtains the Euclid distance D(a, b) between the vector of the detected values and the reference vector. The result is as follows:

$D(X1, S1)=1$ $D(X1, S2)=3$ $D(X2, S1)=5$ $D(X2, S2)=1$.

Further, the signal processing device 12 determines the relation between the calculated Euclid distance D and a threshold value. When the threshold value is made 2, it is determined that X1 is close to the distribution of the state of S1 since the Euclid distance D with respect to S1 is the threshold or less and the Euclid distance D with respect to S2 is the threshold or more. In this way, the signal processing device 12 determines that X1 is the recycled paper. Similarly, it is determined that X2 is close to the distribution of the state of S2, and the signal processing device 12 determines that X2 is the glossy paper.

According to the above example, the raw data of the detected values or the relative values are used, and even if the number of columns is increased, it is possible to determine the record medium 16.

Second Application Example

The signal processing device 12 first expresses detected values, that is, a distribution state by a vector. Each component may be a relative value of the detected value or a binarized numerical value of 0 or 1. A column represents a position on the sensor 14A.

In the case where there are eight detection positions and the binarized values are used, an example of a vector Xk of the detected values becomes $X1=(0,1,0,0,1,1,0,0)$ $X2=(0,0,1,1,1,1,1,0)$.

Here, a vector as reference, that is, an example of a previously determined distribution state is made $S1=(0,1,0,0,1,0,0,0)$:recycled paper $S2=(0,1,1,1,1,1,1,0)$:glossy paper.

The values are stored in a memory of the signal processing device 12 as a table or a part of a program.

Next, a difference H(a, b) between two points $a(a1, a2, \ldots, an)$ $b(b1, b2, \ldots, bn)$ is defined as indicated below.

$$H(a, b) = \sum_{i=1}^{n} (ai - bi)$$

Next, the signal processing device 12 sequentially obtains the difference H(a, b) between the vector of the detected values and the reference vector. The result is as follows:

$H(X1, S1)=+1$ $H(X1, S2)=-2$ $H(X2, S1)=+3$ $H(X2, S2)=-1$

Further, the signal processing device 12 determines the relation between the calculated difference H and a threshold range. When the threshold range R is made $-1 \leq R \leq +1$, the difference H between X1 and S1 is within the threshold range, and the difference H between X1 and S2 is outside the threshold range, and therefore, it is possible to determine that X1 is close to the distribution of the state of S1. In this way, the signal processing device 12 determines that X1 is the recycled paper. Similarly, it is possible to determine that X2 is close to the distribution of the state of S2, and the signal processing device 12 determines that X2 is the glossy paper.

According to the above example, the raw data of the detected values or the relative values are used, and even if the number of columns is increased, it is possible to determine the record medium 16.

Third Application Example

When the record medium 16 is being conveyed, the laser light source 13 irradiates the laser light 17 to the record medium 16 for a definite time. At this time, the line sensor 14 receives the reflected light 18 of the laser light 17 from the record medium 16 for the definite time, and outputs an output signal converted into an electric signal to the signal processing device 12.

The signal processing device 12 first expresses detected values, that is, a distribution state by a vector. Each component may be a relative value of the detected value or a binarized numerical value of 0 or 1. A column represents a position on the sensor 14A.

In the case where there are eight detection positions and the binarized values are used, an example of a vector Xt of the detected values detected at time t is $X1=(0,1,0,1,1,1,1,0)$ $X2=(0,0,1,1,1,1,1,0)$ $X3=(0,1,0,1,1,1,1,0)$.

Next, when detection is performed i times for the definite time, an integrated value I of the detected values $a1(a11, a21, \ldots, an1)$ $a2(a12, a22, \ldots, an2)$ $ai(a1i, a2i, \ldots, ani)$ is defined as indicated below. That is, the detected value is added at each detection position, and a vector is calculated.

$$I = \left(\sum_{k=1}^{i} a1k, \sum_{k=1}^{i} a2k, \ldots, \sum_{k=1}^{i} ank\right)$$

Next, the signal processing device 12 sequentially obtains the integrated value I of the vector of the detected values. An example of the result is as follows:

$I=(0,2,1,3,3,3,3,0)$.

This integrated value I is compared with the reference vector in accordance with the procedure described in the first application example or the second application example, and the kind of the record medium 16 is determined.

According to the example, the raw data of the detected values or the relative values are used, and even if the number of columns is increased, it is possible to determine the record medium 16.

Fourth Application Example

When the record medium 16 is being conveyed, the laser light source 13 irradiates the laser light 17 to the record medium 16 for a definite time. At this time, the line sensor 14 receives the reflected light 18 of the laser light 17 from the record medium 16 for the definite time, and outputs an output signal converted into an electric signal to the signal processing device 12.

The signal processing device 12 first expresses detected values, that is, a distribution state by a vector. Each component may be a relative value of the detected value or a binarized numerical value of 0 or 1. A column represents a position on the sensor 14A.

In the case where there are eight detection positions and the binarized values are used, an example of a vector Xt of the detected values detected at time t is $X1=(0,1,0,1,1,1,1,0)$ $X2=(0,0,1,1,1,1,1,0)$ $X3=(0,1,0,1,1,1,1,0)$.

Next, when detection is performed i times for the definite time, an average value B of the detected values $a1(a11, a21, \ldots, an1)$ $a2(a12, a22, \ldots, an2)$ $ai(a1i, a2i, \ldots, ani)$ is defined as indicated below. That is, the detected value is added at each detection position, and the result is divided by the number of detections to obtain an average value at each detection position, and the vector is calculated.

$$B = \left(\frac{1}{i}\sum_{k=1}^{i} a1k, \frac{1}{i}\sum_{k=1}^{i} a2k, \ldots, \frac{1}{i}\sum_{k=1}^{i} ank\right)$$

Next, the signal processing device 12 sequentially obtains the average value B of the vector of the detected values. An example of the result is as follows:

$B=(0,0.66,0.33,1,1,1,0)$.

When a value less than 1 is rounded to 0, this becomes as follows:

$Br=(0,0,0,1,1,1,1,0)$.

This average value Br is compared with the reference vector in accordance with the procedure described in the first application example or the second application example, and the kind of the record medium 16 is determined.

According to the example, the raw data of the detected values or the relative values are used, and even if the number of columns is increased, it is possible to determine the record medium 16.

Figure 8:
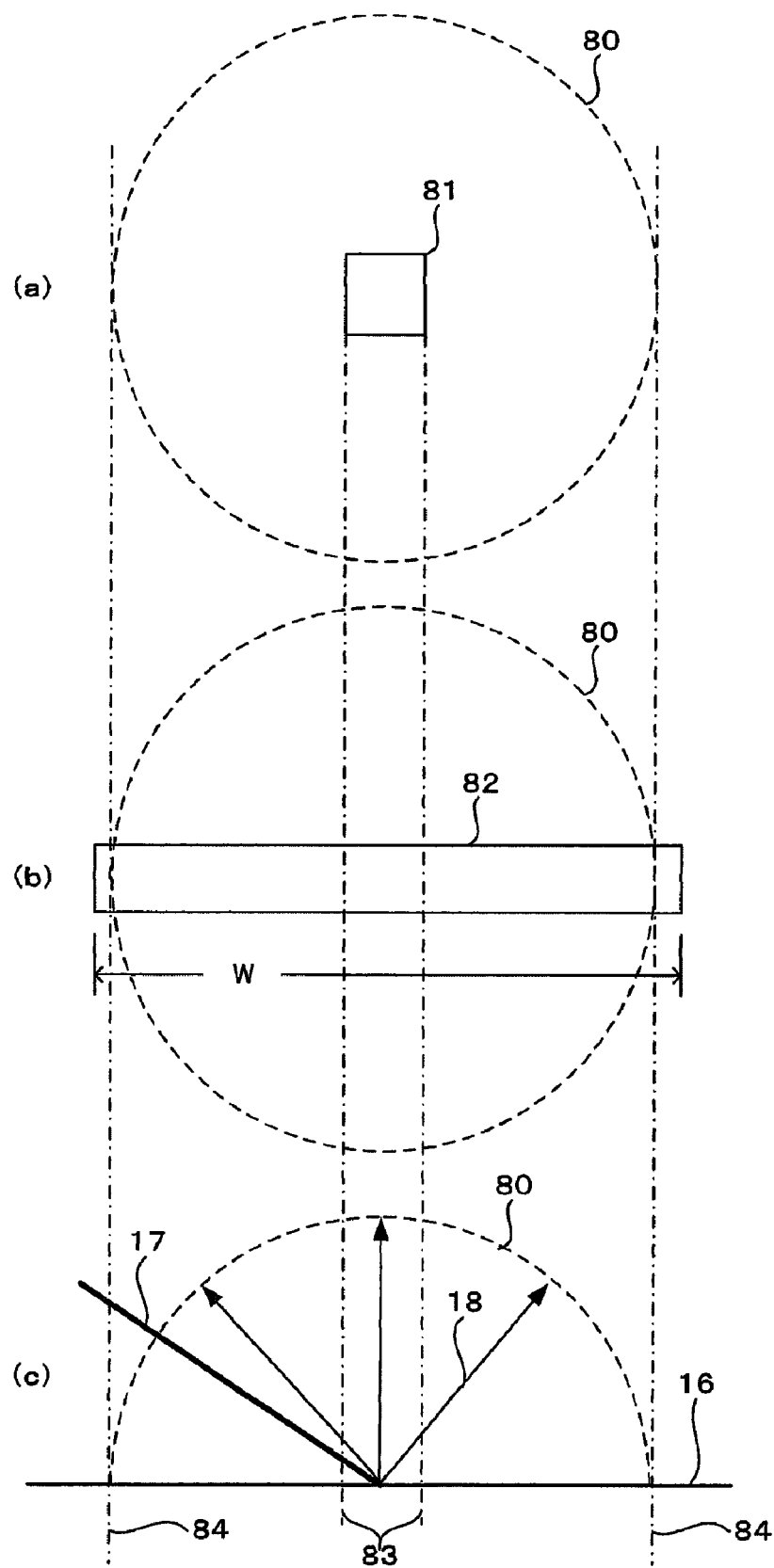
FIG. 8 is a view in which ranges where reflected light can be detected are compared.

Next, a superior point obtained by using the line sensor 14 in this embodiment will be described. FIG. 8 is a view showing comparison of ranges in which the reflected light 18 can be detected.

FIG. 8(c) is a view showing a state, seen from side, where the laser light 17 is irradiated to the record medium 16 and the reflected light 18 is generated. A dotted line 80 indicates the range of scatter of the reflected light 18 and the range where the reflected light 18 is detected by a light detector such as the line sensor 14 or an area sensor.

FIG. 8(a) is a view showing a range 81 of the reflected light 18 which can be detected by the area sensor. Besides, FIG. 8(b) is a view showing a range 82 of the reflected light 18 which can be detected by the sensor 14A of the line sensor 14. Reference character W denotes the length of the sensor 14A of the line sensor 14 in the longitudinal direction as shown in FIG. 3.

As a position approaches the periphery of the dotted line 80, the existence of the reflected light 18 and its intensity reflect the state of the surface of the record medium 16 sensitively. This is also shown in the drawings shown in FIGS. 5 to 7. Accordingly, in the device to determine the kind of the record medium 16 by detecting the reflected light 18, it can be said that when the reflected light 18 is detected in a wider range, the determination accuracy becomes high.

Here, when FIG. 8(a) and FIG. 8(b) are compared with each other, it is understood that the range 82 in which the reflected light 18 can be detected in the case where the line sensor 14 is used, that is, the range indicated by an alternate long and short dash line 84 is wider than the range 81 where the reflected light 18 can be detected in the case where the area sensor is used, that is, the range indicated by an alternate long and short dash line 83, and the detection can be made to the vicinity of the dotted line 80.

Accordingly, the detection accuracy of the record medium becomes higher when the line sensor is used than when the area sensor is used.

The record medium determining device 1 of the embodiment can be installed in the image forming apparatus. In the case where it is installed in the image forming apparatus, for example, the structure can be made as follows. It is desirable that the record medium determining device 1 is set at a position where the laser light 17 from the laser light source 13 can be irradiated to the record medium 16, and a light other than the light from the laser light source 13 is less incident on the line sensor 14. The determination result of the record medium by the record medium determining device 1 is outputted to a control unit of the image forming apparatus, and the control unit of the image forming apparatus adjusts the printing method in accordance with this determination result. Besides, the control unit of the image forming apparatus is constructed to control the operation of the record medium determining device 1.

As described above, in this embodiment, the record medium determining device 1 irradiates the laser light 17 to the surface of the record medium 16, the received light position and the received light intensity of the reflected light 18 are detected by the line sensor 14, and the kind of the record medium 16 is determined by comparing the distribution state of the received light position and the received light intensity with the previously determined distribution state. Thus, the range where the reflected light 18 can be detected is widened, and there is an effect that more kinds of the record medium 16 can be determined with high accuracy.

<Image Forming Apparatus>

Next, the image forming apparatus will be described.

Figure 9:
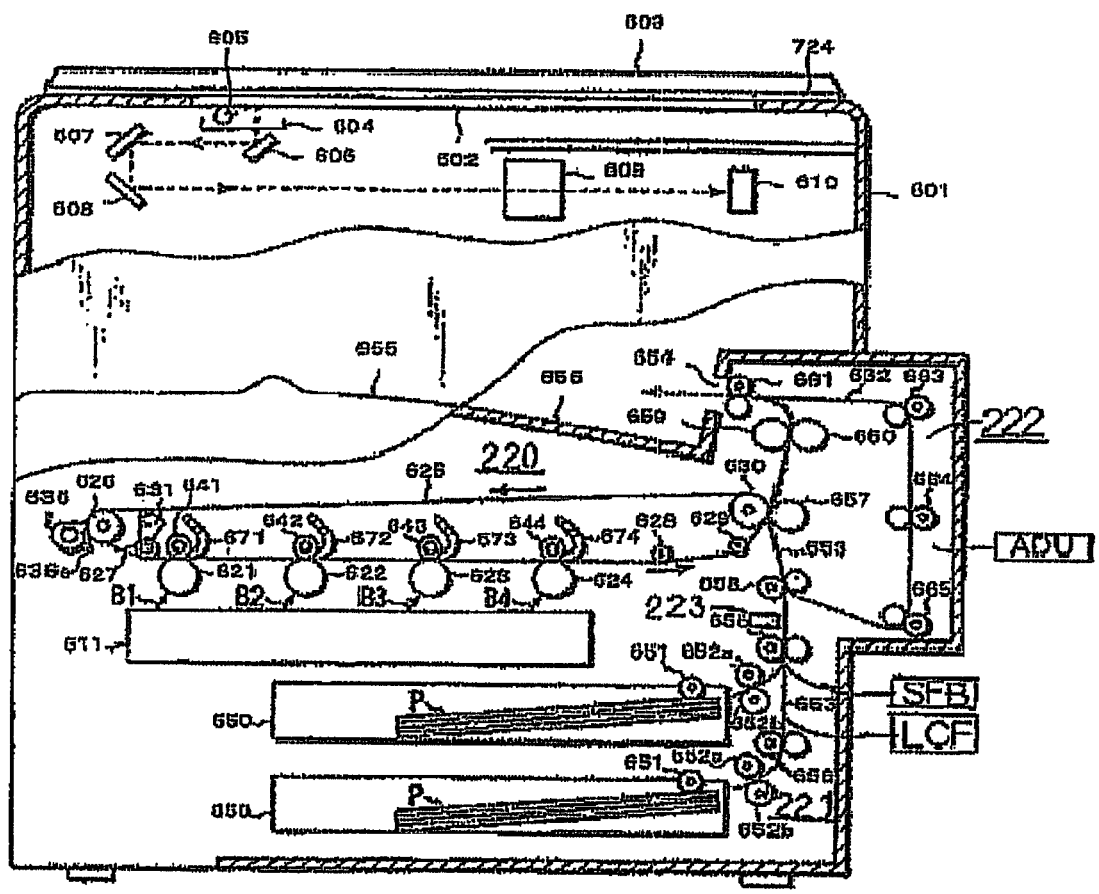
FIG. 9 is a view showing a structural example of an image forming apparatus.

FIG. 9 is a view showing a structural example of the image forming apparatus. As shown in FIG. 9, a document stand 602 for mounting documents, which is formed of a transparent material such as a glass plate, is provided at an upper part of an apparatus main body 601. A cover 603 is openably and closably mounted on the apparatus main body 601 so as to cover the document stand 602.

A scan unit (not shown) to optically read an image of an original document mounted on the document stand 602 is provided at the lower side of the document stand 602 in the inside of the apparatus main body 601. For example, the scan unit includes a carriage 604, reflecting mirrors 606, 607 and 608 to reflect a light of an exposure lamp 605 reflected by the original document, a scaling lens block 609 to scale the reflected light, and a CCD (Charge Coupled Device) 610. The carriage 604 is provided with the exposure lamp 605 to irradiate the light to the document stand 602, and is constructed to be capable of reciprocating along the lower surface of the document stand 602.

The carriage 604 moves while the exposure lamp 605 is being turned on, so that the original document mounted on the document stand 602 is exposed. A reflected light image of the original document, which is mounted on the document stand 602, by the exposure is projected onto the CCD 610 through the reflecting mirrors 606, 607 and 608 and the scaling lens block 609. The CCD 610 outputs an image signal corresponding to the projected reflected light image of the original document.

An image forming unit 220 is provided below the scan unit in the inside of the apparatus main body 601. The image forming unit 220 includes, for example, a print engine (not shown) and a process unit (not shown).

The print engine includes an exposure unit 611. The process unit includes photoconductive drums 621, 622, 623 and 624 arranged along the exposure unit 611, an endless transfer belt 625 arranged to be opposite to the exposure unit 611 across the photoconductive drums 621, 622, 623 and 624, a drive roller 626 to drive the transfer belt 625, primary transfer rollers 641, 642, 643 and 644 arranged to be opposite to the photoconductive drums 621, 622, 623 and 624 across the transfer belt 625, and a transfer roller drive unit to drive the primary transfer rollers 641, 642, 643 and 644.

The transfer belt 625 is stretched over a drive roller 626, guide rollers 627, 628 and 629 and a driven roller 630, receives power from the drive roller 626 and rotates and runs in the counterclockwise direction. The guide roller 627 is provided to be freely moved up and down, and receives the rotation of a cam 631 to be moved to the transfer belt 625 side. By this, the guide roller 627 displaces the transfer belt 625 to the side of the photoconductive drums 621, 622, 623 and 624.

The image forming unit 220 executes an image formation process to form an image based on image data (image signal outputted from the CCD 610) and to print the image on the record medium being conveyed. That is, after the image signal outputted from the CCD 610 is suitably processed, it is supplied to the exposure unit 611. The exposure unit 611 emits a laser beam B1 corresponding to a yellow color image signal to the photoconductive drum 621 for yellow, emits a laser beam B2 corresponding to a magenta color image signal to the photoconductive drum 622 for magenta, emits a laser beam B3 corresponding to a cyan color image signal to the photoconductive drum 623 for cyan, and emits a laser beam B4 corresponding to a black color image signal to the photoconductive drum 624 for black.

The primary transfer rollers 641, 642, 643 and 644 are moved (lowered) to the transfer belt 625 side, so that the transfer belt 625 is brought into contact with the photoconductive drums 621, 622, 623 and 624, and visible images on the photoconductive drums 621, 622, 623 and 624 are transferred to the transfer belt 625.

A not-shown drum cleaner, a charge-removal lamp, a charging unit, and a developing unit are sequentially disposed around the photoconductive drum 621. The drum cleaner includes a drum cleaning blade which comes in contact with the surface of the photoconductive drum 621, and scrapes away a developer remaining on the surface of the photoconductive drum 621 by the drum cleaning blade.

The charge-removal lamp removes a charge remaining on the surface of the photoconductive drum 621. The charging unit applies a high voltage to the photoconductive drum 621, so that the surface of the photoconductive drum 621 is charged with an electrostatic charge. The laser beam B1 emitted from the exposure unit 611 is irradiated to the surface of the charged photoconductive drum 621. An electrostatic latent image is formed on the surface of the photoconductive drum 621 by this irradiation. The developing unit supplies a yellow developer (toner) to the surface of the photoconductive drum 621, so that the electrostatic latent image on the surface of the photoconductive drum 621 is made a visible image.

Also in the other photoconductive drums 622, 623 and 624, similarly, developers of the corresponding colors are used and electrostatic latent images on the surfaces of the respective photoconductive drums 622, 623 and 624 are made visible images.

A cleaner 636 is provided at a position opposite to the drive roller 626 of the image forming unit 220 across the transfer belt 625. This cleaner 636 includes a cleaning blade 636a which comes in contact with the transfer belt 625, and scrapes away the developer remaining on the transfer belt 625 by the cleaning blade 636a.

The printing mode is changed as described below. Hooks 671, 672, 673 and 674 are provided in the vicinities of the primary transfer rollers 641, 642, 643 and 644. The hooks 671, 672, 673 and 674 are engaged with shafts of the primary transfer rollers 641, 642, 643 and 644 to raise the shafts while rotating, and move the primary transfer rollers 691, 642, 643 and 644 in the direction of separating from the photoconductive drums 621, 622, 623 and 624. The printing mode, such as a full-color mode, all separation mode or a monochrome mode, is changed by not moving any of the primary transfer rollers 641, 692, 643 and 644 or by moving them and changing the combination.

Next, a containing mechanism and a supply mechanism of record media will be described. Plural record medium cassettes 650 to contain record media are provided below the exposure unit 611. In these record medium cassettes 650, a number of record media P different from one another in record medium type are contained in a stacked state. A record medium supply mechanism 221 to supply the record medium in the record medium cassette 650 one by one from above is provided at an exit portion (right in the drawing) of each of the record medium cassettes 650. By this record medium supply mechanism 221, the record medium P is taken out one by one from any one of the record medium cassettes 650. The record medium supply mechanism 221 for taking out includes a pickup roller 651, a record medium supply roller 652a, and a separating roller 652b, separates the record medium P, which is taken out from the record medium cassette 650, one by one, and supplies it to a record medium conveyance path 653.

Next, the conveyance path of the record medium will be described. The record medium conveyance path 653 extends to an upper record medium discharge port 654 through the driven roller 630 of the image forming unit 220. The record medium discharge port 654 faces a record medium discharge unit 655 continuous with the outer peripheral surface of the apparatus main body 601. At the starting end side of the conveyance path 653, a conveyance roller 656 is provided in the vicinity of each of the record medium supply mechanisms 221. When the record medium is supplied by one of the record medium supply mechanisms 221, the record medium conveyance path 653 conveys the supplied record medium to the record medium discharge unit 655.

A secondary transfer roller 657 is provided at a halfway position of the record medium conveyance path 653 where it is opposite to the driven roller 630 across the transfer belt 625. A register roller 658 is provided at an upstream position of the driven roller 630 and the secondary transfer roller 657 in the conveyance direction.

At the timing in synchronization with the transfer operation as an operation of transferring an image formed with a developer (toner) to the record medium by the transfer belt 625 and the secondary transfer roller 657, the register roller 658 sends the record medium P to between the transfer belt 625 and the secondary transfer roller 657. The secondary transfer roller 657 holds the sheet record medium P sent from the register roller 658 between itself and the transfer belt 625 on the driven roller 630, transfers the visible image formed with the developer (toner) and transferred on the transfer belt 625 to this record medium P, and prints it. As stated above, the register roller 658 conveys the record medium P to the image forming unit 220 including the transfer belt 625 and the secondary transfer roller 657 in synchronization with the transfer operation of the image forming unit 220.

A heat roller 659 for heat fixation and a press roller 660 in contact with the heat roller 659 are provided at a downstream position of the record medium conveyance path 653 with respect to the secondary transfer roller 657. The image transferred on the record medium P is fixed by the heat roller 659 and the press roller 660. Incidentally, a record medium discharge roller 661 is provided at the end of the record medium conveyance path 653.

An auto duplex unit (hereinafter referred to as ADU) 222 may be provided in the apparatus main body 601. The ADU 222 is installed so as to couple a sub-conveyance path 662, which is a path for conveying the record medium P in the ADU 222, to the end of the record medium conveyance path 653 and an inlet to the register roller 658. The sub-conveyance path 662 branches away from the downstream side (end of the record medium conveyance path 653) of the record medium conveyance path 653 with respect to the image forming unit 220, and meets the upstream side (upstream side position of the register roller 658) of the record medium conveyance path 653 with respect to the image forming unit 220.

The sub-conveyance path 662 reverses the obverse and reverse of the record medium P for two-sided printing. The sub-conveyance path 662 is provided with record medium supply rollers 663, 664 and 665, the ADU 222 reversely sends the record medium P conveyed from the image forming unit 220 to the record medium discharge unit 655, conveys it along the sub-conveyance path 662, and causes it to meet the record medium conveyance path 653 at the upstream side of the image forming unit 220. When the conveyance is made in this way, the obverse and reverse of the record medium P is reversed.

After the record medium P returned to the upstream side of the image forming unit 220 by the sub-conveyance path 662 meets the record medium conveyance path 653, the register roller 658 establishes synchronization with the transfer operation of the image forming unit 220, and the record medium is sent to the transfer position where the transfer belt 625 is in contact with the secondary transfer roller 657. As stated above, the visible image on the transfer belt 625 is transferred also to the reverse surface of the record medium P and is printed.

When the two-sided printing is specified by the operation panel 724 provided on the apparatus main body 601 or the computer connected to the apparatus main body 601 through the network, the sub-conveyance path 662 of the ADU 222 is brought into the state of performing the operation to reverse the obverse and reverse of the record medium P.

Next, an additionally provided device will be described. In the example of the apparatus main body 601 shown in FIG. 9, the two record medium cassettes 650 are provided as the supply source of the record medium. Three or more record medium cassettes 650 may be provided in the apparatus main body 601. In addition, although not shown, a manual feed record medium supply mechanism such as a Stack Feed Bypass (hereinafter referred to as SFB), or a large capacity record medium feeder (hereinafter referred to as LCF), which can contain several thousand record media in a stacked form, can also be provided. The SFB or the LCF is installed in the apparatus main body 601 so that the path to supply the record medium meets the record medium conveyance path 653.

Figure 10:
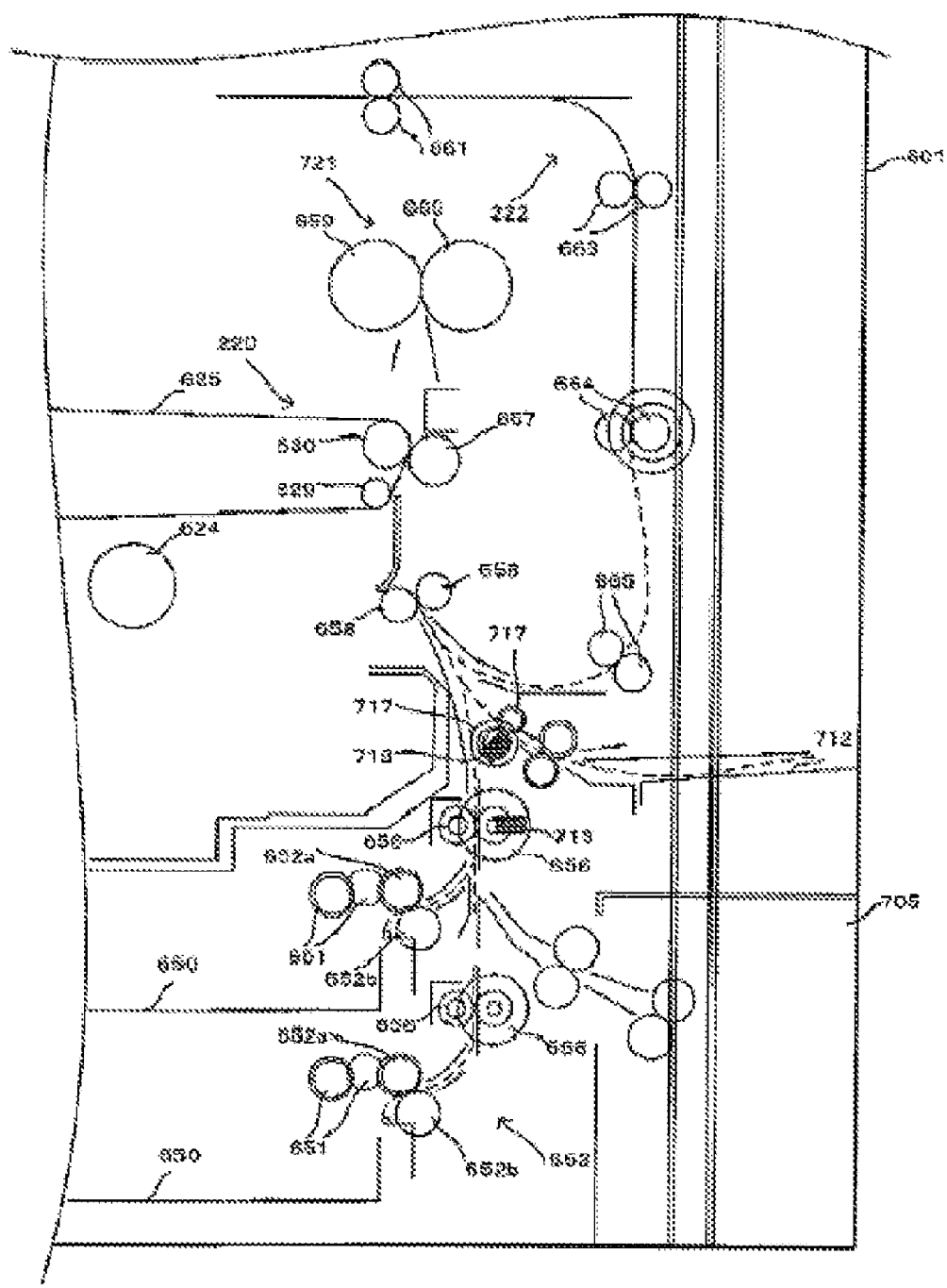
FIG. 10 is a view showing the vicinity of a record medium conveyance path in detail.

Next, the installation position of the record medium determining device 1 of the embodiment will be described. FIG. 10 is a view showing the vicinity of the record medium conveyance path 653 in detail. Hereinafter, a combination of the heat roller 659 and the press roller 660 is called a fixing unit 721. In this fixing unit 721, the heat roller 659 heats the record medium P on which the developer (toner) is transferred, and the press roller 660 conveys it while applying pressure, so that the developer is fixed to the record medium P.

The apparatus main body 601 is provided with a not-shown control unit. This control unit can be constructed of, for example, a CPU, a memory such as a ROM or a RAM, an LSI and the like. The control unit controls the temperature of the heat roller 659. For example, in the case where there is no signal from the control unit, the heat roller 659 keeps a previously determined temperature according to the kind of the record medium P and is on standby, and in the case where a signal of fixation start is received, the temperature is changed in accordance with the instruction.

Since the apparatus main body 601 has the structure as stated above and fixes the developer, the record medium determining device 1 is disposed on the upstream side of the record medium conveyance path 653 with respect to the fixing unit 721.

In the case where only one record medium determining device 1 is used, it is installed at a first installation position 223 shown in FIG. 9. The first installation position 223 is the upstream side of the record medium conveyance path 653 with respect to the image forming unit 220, and is the upstream side position of the register roller 658. In the case where the SFB 712 or the LCF 705 is installed, the first installation position 223 is the downstream side position of the meeting point between the record medium supply path from the SFB 712 and the LCF 705 and the record medium conveyance path 653. The record medium determining device 1 is installed to face the surface of the record medium to be conveyed.

The record medium determining device 1 is arranged at the first installation position 223, so that the one record medium determining device 1 can detect the kinds of the record media P conveyed on the record medium conveyance path 653 from all record medium supply sources.

According to the model of the image forming apparatus, there is a case where the installation can not be performed at the first installation position 223 according to the relation of the arrangement of various parts in the inside of the apparatus main body 601. Besides, there is also a model in which the SFB 712 is attached as an option. In these cases, the record medium determining device 1 can also be disposed at the following two places.

A description will be made by use of FIG. 10. A second installation position 715 is a position in the record medium conveyance path 653, on the upstream side of the record medium conveyance path 653 with respect to the image forming unit 220 and on the upstream side of the register roller 658 and is a position on the downstream side with respect to the record medium supply roller 652a and the separating roller 652b of the uppermost stage cassette device 650, and on the downstream side of the meeting position between the record medium supply path from the LCF 705 and the record medium conveyance path 653. The record medium determining device 1 is disposed to face the surface of the record medium to be conveyed. The record medium determining device 1 may be installed in the vicinity of the conveyance roller 656 at the second installation position 715.

A third installation position 718 is a position on the upstream side of the meeting position between the record medium supply path from the SFB 712 and the record medium conveyance path 653. The record medium determining device 1 is installed to face the surface of the record medium to be conveyed. The record medium determining device 1 may be installed in the vicinity of a conveyance roller 717 at the third installation position 718.

When the record medium determining device 1 is disposed at the second installation position 715 and the third installation position 718, in the model in which the SFB 712 is attached as an option, there is an effect that the record medium determining device 1 can be installed at the installation position 718 as the need arises.

Next, a description will be given to an application example relating to the processing of a signal of determination result outputted from the record medium determining device 1. An operation panel 724 which selects the kind of the record medium P and is also used for display of information and for input at the time of data setting is attached to the upper surface of the apparatus main body 601. The operation panel 724 is connected to the control unit. The control unit controls the speed of a motor to rotate and drive each roller for conveying the record medium, and performs also the stop and restart of conveyance of the record medium.

First, the control unit stores the default kind of the record medium or the kind of the record medium inputted by the operation panel 724 into the memory as the set record medium, and sets the standby temperature of the heat roller 659 according to the set record medium.

Next, the record medium P is conveyed, and when the record medium determining device 1 determines the kind of the record medium P, the record medium determining device 1 outputs a signal of determination result to the control unit. In accordance with the determination result, the control unit sets, for example, the conveyance speed of the record medium, the rotation speed of the fixing unit 721, and the temperature of the heat roller 659 at the time of fixing, and transmits instructions to these devices.

As stated above, the image forming apparatus of this application example first sets the set record medium, and next, further sets the conditions, such as the speed at the time of fixing and the temperature, in accordance with the kind of the record medium determined by the record medium determining device 1. Thus, there is an effect that the finer condition setting at the time of fixing according to the kind of the record medium and the execution of the fixing can be quickly performed.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An image forming apparatus to form an image on a record medium, comprising:
 a record medium supply mechanism to supply a record medium one by one;
 a record medium conveyance path to convey the record medium supplied from the record medium supply mechanism to a record medium discharge unit;
 a laser light source to irradiate a laser light to a surface of a record medium;
 a line sensor which has plural optical sensors for the laser light source to receive a reflected light of the laser light from the record medium to output an output signal converted into an electric signal,
 when the record medium totally reflects the laser light, the line sensor is arranged so that an axis of a sensor of the line sensor in a longitudinal direction is positioned on a plane to which a light path of the laser light irradiated from the laser light source and reflected by the record medium belongs;

a signal processing device to determine a kind of the record medium based on the output signal; and an image forming unit that is arranged on a downstream side of the record medium conveyance path with respect to the line sensor and forms an image to the record medium conveyed through the record medium conveyance path;

when the record medium is being conveyed, the laser light source irradiates the laser light to the record medium for a definite time, the line sensor receives the reflected light of the laser light from the record medium for the definite time and outputs the output signal converted into the electric signal, and the signal processing device compares a distribution state of an average of the received light intensity for the definite time at the received light position with a previously determined distribution state, and determines the kind of the record medium.

2. The apparatus according to claim 1, wherein a length of a sensor of the line sensor in a longitudinal direction is not less than 5 mm and is not larger than a length of a maximum record medium to be determined in the longitudinal direction.

3. A method of image forming of an image forming apparatus, comprising;

supplying a record medium one by one from a record medium supply mechanism;

conveying the record medium supplied from the record medium supply mechanism to a record medium discharge unit through a record medium conveyance path;

irradiating a laser light to a surface of a record medium from a laser light source;

receiving a reflected light of the laser light from the record medium to output an output signal converted into an electric signal with a line sensor which has plural optical sensors, when the record medium totally reflects the laser light, the line sensor is arranged so that an axis of a sensor of the line sensor in a longitudinal direction is positioned on a plane to which a light path of the laser light irradiated from the laser light source and reflected by the record medium belongs;

determining a kind of the record medium based on the output signal with a signal processing device to; and forming an image to the record medium conveyed through the record medium conveyance path with an image forming unit that is arranged on an downstream side of the record medium conveyance path with respect to the line sensor;

when the record medium is being conveyed, the laser light source irradiates the laser light to the record medium for a definite time, the line sensor receives the reflected light of the laser light from the record medium for the definite time and outputs the output signal converted into the electric signal, and the signal processing device compares a distribution state of an average of the received light intensity for the definite time at the received light position with a previously determined distribution state, and determines the kind of the record medium.

* * * * *